US 8,352,390 B2

(12) United States Patent
Yuta

(10) Patent No.: US 8,352,390 B2
(45) Date of Patent: *Jan. 8, 2013

(54) METHOD, PROGRAM, AND APPARATUS FOR GENERATING TWO-CLASS CLASSIFICATION/PREDICTION MODEL

(75) Inventor: Kotaro Yuta, Narashino (JP)

(73) Assignee: Fujitsu Limited, Kawasaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/795,078

(22) Filed: Jun. 7, 2010

(65) Prior Publication Data

US 2010/0241598 A1 Sep. 23, 2010

Related U.S. Application Data

(63) Continuation of application No. PCT/JP2007/074334, filed on Dec. 18, 2007.

(51) Int. Cl.
*G06F 15/18* (2006.01)
(52) U.S. Cl. ............................................. 706/13
(58) Field of Classification Search .................... 706/12, 706/20, 13
See application file for complete search history.

(56) References Cited

U.S. PATENT DOCUMENTS

| | | | |
|---|---|---|---|
| 6,219,658 B1 | 4/2001 | Gordon | |
| 7,725,413 B2 * | 5/2010 | Yuta | 706/20 |
| 2009/0222390 A1 * | 9/2009 | Yuta | 706/13 |

FOREIGN PATENT DOCUMENTS

| | | |
|---|---|---|
| JP | 5-143636 | 6/1993 |
| WO | 2004/097408 A1 | 11/2004 |

OTHER PUBLICATIONS

Kohtaro Yuta, "Development of K-step Yard Sampling Method and its Application to ADME-T Predictions", 34th Structure Activity Correlation Symposium, Nov. 7, 2006, pp. 29-30.
Kohtaro Yuta, "Chemical Data Anaylsis Techniques by Tailor-Made Modeling", 30th Symposium on Chemical Information, Nov. 8, 2007, pp. 37-38.
Tatsuya Nishino et al., "Active QSAR Modeling Based on Structure Similarity," The 21st Annual Conference of the Japanese Society for Artificial Intelligence, 3D7-4, Jun. 2007, pp. 1-2.

(Continued)

*Primary Examiner* — Jeffrey A Gaffin
*Assistant Examiner* — Ola Olude Afolabi
(74) *Attorney, Agent, or Firm* — Staas & Halsey LLP

(57) ABSTRACT

A two-class classification/prediction model is generated in a simple operation by performing two-class classification with a classification rate substantially close to 100%. The two-class classification/prediction model is generated by a) obtaining a discriminant function for classifying a training sample set into two predetermined classes on the basis of an explanatory variable generated for each sample contained in the training sample set, b) calculating a discriminant score for each training sample by using the obtained discriminant function, c) determining, based on the calculated discriminant score, whether the training sample is correctly classified or not, d) determining a misclassified-sample region based on maximum and minimum discriminant scores taken from among misclassified samples in the training sample set, e) constructing a new training sample set by extracting the training samples contained in the misclassified-sample region, and f) repeating a) to e) for the new training sample set.

20 Claims, 13 Drawing Sheets

OTHER PUBLICATIONS

English language International Search Report for PCT/JP2007/074334, mailed on Mar. 4, 2008.
Robert Tibshiran et al., "Margin Trees for High-dimensional Classification", Journal of Machine Learning Research, vol. 8, Mar. 2007, pp. 637-652.
André Gohr, "4 Linear Models for Classification 4.1 Discriminant Functions", Institute of Computer Science, Feb. 2007, Martin-Luther Universität, Halle-Wittenburg, DE, 19 pp.
Yuta K, "K-step Yard sampling method no Kaihatsu to ADME-T Yosoku eno Tekiyo" Kozo Kassei Sokan Symposium Koen Yoshisu, vol. 34, Nov. 2006, pp. 29-30.
Yuta K, "Green Chemistry to ADMEWORKS", Fujitsu, vol. 54, No. 6, Nov. 2003, pp. 471-479, Abstract.
European Search Report dated May 9, 2011 in corresponding European Patent Application 07850820.7.
First Chinese Office Action issued Jul. 4, 2012 in corresponding Chinese Patent Application No. 200780101995.9.

* cited by examiner

FIG. 5

| | A Structure | B CAS Number | C Ames test |
|---|---|---|---|
| 1 | | 994-05-8 | nonmutagen (−) |
| 2 | | 99-82-1 | nonmutagen (−) |
| 3 | | 99-76-3 | nonmutagen (−) |
| 4 | | 98-00-0 | mutagen (+) |
| 5 | | 97-56-1 | mutagen (+) |

F I G . 6

| | A Structure | B Molecular Mass (Whole Molecule) | C Molecular Surface Area (Whole Molecule) | D Molecular Volume (Whole Molecule) | E Kappa 1 index (Whole Molecule) | F log P (Whole Molecule) | G Shape Flexibility index (Whole Molecule) | H Randic Topological index (Whole Molecule) |
|---|---|---|---|---|---|---|---|---|
| 1 | | 102.2 (x11) | 143.704 (x21) | 91.8144 (x31) | 7 | 1.3154 | 2.30088 | 3.12132 |
| 2 | | 140.3 (x12) | 190.412 (x22) | 129.174 (x32) | 8.1 | 3.7656 | 2.76071 | 4.69838 |
| 3 | | 152.16 (x13) | 172.868 | 101.168 | 9.09091 | 1.4923 | 2.35543 | 5.23638 |
| 4 | | 98.11 (x14) | 120.712 | 68.9598 | 5.14286 | 0.4597 | 1.24264 | 3.43185 |
| 5 | | 123.17 (x15) | 152.166 | 89.6854 | 7.11111 | | 1.48936 | 4.18154 |

F I G. 7
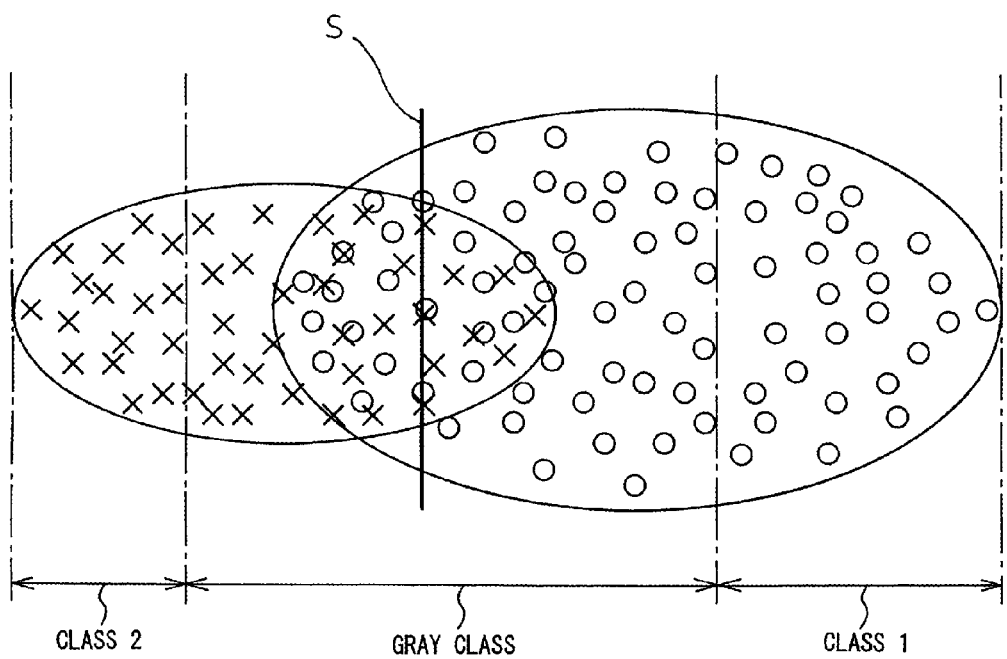

F I G. 9

| STAGE | DISCRIMINANT FUNCTION | GRAY ZONE INFORMATION |
|---|---|---|
| STAGE 1 | DISCRIMINANT FUNCTION 1 | Yg1(mini), Yg1(max) |
| STAGE 2 | DISCRIMINANT FUNCTION 2 | Yg2(mini), Yg2(max) |
| STAGE 3 | DISCRIMINANT FUNCTION 3 | Yg3(mini), Yg3(max) |
|  |  |  |
|  |  |  |
| STAGE n | DISCRIMINANT FUNCTION n | Ygn(mini), Ygn(max) |

METHOD, PROGRAM, AND APPARATUS FOR GENERATING TWO-CLASS CLASSIFICATION/PREDICTION MODEL

CROSS-REFERENCE TO RELATED APPLICATION

This application is a continuation application based upon International Application No. PCT/JP2007/074334, filed on Dec. 18, 2007, the entire contents of which are incorporated herein by reference.

FIELD

The present invention relates to a method, program, and apparatus for generating a classification/prediction model for samples of unknown classes.

BACKGROUND

A classification problem learns a rule for classifying samples into a predetermined plurality of classes from a set of samples each known to belong to one of the classes, and predicts the class to which a sample of unknown class belongs by using the learned rule as a prediction model. Among others, a two-class classification which classifies a sample set into two classes is the most basic classification, and has long been used in structure-activity relationship research and structure-property relationship research; in recent years, the two-class classification has been attracting attention as a useful technique for testing chemicals for toxicity, etc. Methods for learning rules, i.e., classification methods, include linear discriminant analysis methods, such as linear learning machine, discriminant analysis, Bayes linear discriminant analysis, SVM (Support Vector Machine), AdaBoost, etc., and nonlinear discriminant analysis methods, such as Bayes nonlinear discriminant analysis, SVM (Support Vector Machine+Kernel), neural networks, KNN (K-Nearest Neighbor), decision tree, etc.

Generally, in a classification problem, misclassification is unavoidable, and it is difficult to achieve a classification rate of 100%. The term "classification rate" is a measure that indicates how correctly samples for which the classes they belong to are known have been classified, while "prediction rate" is a measure that indicates how correctly samples for which the classes they belong to are not known have been classified. Basically, the "prediction rate" does not exceed the "classification rate." Accordingly, if the "classification rate" is raised, the upper limit of the "prediction rate" automatically increases. This means that if the classification rate can be raised, the prediction rate improves. Further, from the general characteristics of data analysis, it is well known that as the number of samples used to generate a prediction model increases, the number of misclassified samples also increases and as a result, the classification rate drops. A misclassification is an instance in which a sample that may belong to class 1, for example, is wrongly classified as a sample belonging to class 2. The major reason for this is that as the total number of samples used increases, the absolute number of samples that cause noise in the classification also increases. Unlike statistical techniques, powerful data analysis techniques, such as multivariate analysis or pattern recognition are susceptible to noise, and in most cases, increasing the number of samples will end up making the data analysis difficult.

As a field that requires high classification/prediction rates, the field of chemical toxicity evaluation is gaining importance from the standpoint of environmental protection. In this field, chemicals are often classified into two classes, a toxic chemical group (class 1) and a nontoxic chemical group (class 2), but since the factors contributing to the manifestation of toxicity are complex and diverse, as is always the case in this field, misclassification can easily occur and if the current state of the art of data analysis is applied, it is difficult to raise the classification rate.

It is also to be noted that no matter how high the classification rate is obtained, if the number of samples used is large, the number of misclassified samples becomes large. For example, when classifying toxic chemicals and nontoxic chemicals, if the number of samples used for training is large, for example, if the classification is to be performed using 10000 chemicals, a classification rate of 90% would mean that 1000 chemicals would be misclassified, the number being large enough to become a problem. Further, in the field of toxicity classification, if chemicals having no toxicity were misclassified as chemicals having toxicity (false positive), it would not present a serious problem, but because of the nature of the subject, it would be very dangerous if chemicals having toxicity were misclassified as chemicals having no toxicity (false negative), and such a misclassification should be avoided by all means. From this point also, it is desirable that the classification rate be increased to 100%.

While increasing the prediction rate is the final target of a classification problem, it is now recognized that increasing the classification rate is of utmost concern, and various efforts have been expended for this purpose. As earlier noted, considering the fact that the prediction rate does not exceed the classification rate, if the classification rate is raised, the upper limit of the prediction rate increases. Noting this point, the present inventor has proposed a classification method that can achieve a classification rate as close as possible to 100%, i.e., "K-step Yard sampling method" (hereinafter referred to as the KY method) (Non-patent document 1, PCT/JP-2007/056412).

To briefly describe this method, first a training sample set is constructed using samples known to belong to a first class and samples known to belong to a second class. Then, by performing discriminant analysis on the training sample set, a first discriminant function (hereinafter called the AP model) that achieves a high classification rate, for example, a classification rate of substantially 100%, for the first class and a second discriminant function (hereinafter called the AN model) that achieves a high classification rate, for example, a classification rate of substantially 100%, for the second class are generated. Next, objective variables of each sample are calculated using the two discriminant functions, the AP model and the AN model, and samples for each of which the values of the objective variables, i.e., the classification results, match between the two discriminant functions and samples for each of which the results do not match are identified.

Since the AP and AN models provide a classification rate of nearly 100% for the first and second classes, respectively, any sample whose classification results match between the AP and AN models is identified as a correctly classified sample. Accordingly, any sample whose classification results match is assigned to class 1 or class 2, whichever is identified. On the other hand, any sample whose classification results do not match between the AP and AN models is assigned to a gray class, i.e., a third class where no class determination is made.

When the gray class in the first stage is thus formed, the samples assigned to the gray class are grouped together to form a new sample set. Then, the AP model and the AN model are newly generated for this sample set, and the samples are classified in the same manner as described above. As a result, the gray class in the second stage is formed; thereafter, the gray class in the third stage, the gray class in the fourth stage, etc., are formed in a similar manner. By repeating the gray class formation until the number of samples assigned to the gray class finally decreases to zero, all the samples can be correctly classified into the first and second classes, respectively. That is, a classification rate of 100% is achieved.

Non-patent document 1: "Development of K-step Yard Sampling Method and its Application to ADME-T Predictions," 34th Structure-Activity Correlation Symposium, November 2006

Non-patent document 2: "Chemical Data Analysis Techniques by Tailor-Made Modeling," 30th Symposium on Chemical Information, November 2007

SUMMARY

As described above, the KY method can almost achieve a classification rate of 100% for any training sample set, and therefore this method is far more useful than conventional techniques in achieving perfect classification. However, with this method, two special discriminant functions, i.e., the AP model and the AN model, may be generated in order to identify gray class samples in each stage. As a result, the method has the disadvantage that the number of samples increases and, if the number of stages for analysis increases, for example, to several tens, the time and labor taken to construct the model will be enormous. Furthermore, the computation time needed for classification/prediction also increases, thus placing a great burden on users who want to perform classification/prediction using this model.

The present invention has been devised to overcome the above-described problem associated with the prior art, and an object of the invention is to provide a method, program, and apparatus for generating a classification/prediction model that can ensure a nearly perfect classification rate, while facilitating the generation of the model.

To solve the above problem, the present invention provides a method for generating a two-class classification/prediction model, comprising: a) obtaining a discriminant function for classifying a training sample set into two predetermined classes on the basis of an explanatory variable generated for each individual training sample contained in the training sample set; b) calculating a discriminant score for each training sample by using the obtained discriminant function; c) based on the calculated discriminant score, determining whether the training sample is correctly classified or not; d) determining a misclassified-sample region based on maximum and minimum discriminant scores taken from among misclassified samples in the training sample set; e) constructing a new training sample set by extracting the training samples contained in the misclassified-sample region; f) repeating a) to e) for the new training sample set; and g) storing, as a two-class classification/prediction model for samples of unknown classes, a plurality of discriminant functions obtained as a result of the repetition and misclassified-sample region information associated with each of the discriminant functions.

In the above method, the misclassified-sample region in d) may be determined by adding an arbitrary safety margin on each side of the maximum and minimum discriminant scores taken from among the misclassified training samples. Further, the classification may be terminated when the number of misclassified training samples has decreased to zero in c).

In the above method, f) may repeat a) to e) a predetermined number of times. Further, the method may include removing unnecessary explanatory variables by performing feature extraction on the explanatory variables generated for the training sample set.

To solve the above problem, the present invention also provides a program for generating a two-class classification/prediction model, the program causing a computer to: a) obtain a discriminant function for classifying a training sample set into two predetermined classes on the basis of an explanatory variable generated for each individual training sample contained in the training sample set; b) calculate a discriminant score for each training sample by using the obtained discriminant function; c) based on the calculated discriminant score, determine whether the training sample is correctly classified or not; d) determine a misclassified-sample region based on maximum and minimum discriminant scores taken from among misclassified samples in the training sample set; e) construct a new training sample set by extracting the training samples contained in the misclassified-sample region; and f) repeat a) to e) for the new training sample set.

To solve the above problem, the present invention also provides an apparatus for generating, from a training sample set constructed from a plurality of samples each known to belong to class 1 or class 2, a two-class classification/prediction model for classifying an unknown sample which is not known to belong to the class 1 or the class 2, comprising: an explanatory variable acquiring device which acquires an explanatory variable for each sample contained in the training sample set; a discriminant function generating engine which generates a discriminant function for discriminating between the class 1 and the class 2 by performing discriminant analysis based on the acquired explanatory variable; a discriminant score calculation device which calculates a discriminant score for each sample based on the generated discriminant function; a sample set generating device which determines a misclassified-sample region based on the calculated discriminant score, and generates a new sample set by extracting samples contained in the region; a control device which causes the explanatory variable acquiring device, the discriminant function generating engine, the discriminant score calculation device, and the sample set generating device to operate repeatedly by using the generated new sample set as the training sample set; and a storage device which stores, as the classification/prediction model, the discriminant function generated by the discriminant function generating engine and information concerning the misclassified-sample region determined by the sample set generating device.

The present invention determines, from the discriminant scores of the samples obtained by the generated discriminant function, the misclassified-sample region in the pattern space formed by the discriminant function. More specifically, the misclassified-sample region, i.e., the gray zone, is determined based on the maximum and minimum discriminant scores of the samples misclassified by the generated discriminant function. As a result, all of the samples whose discriminant scores fall between the maximum and minimum values can be identified as gray-class samples. That is, the present invention requires the use of only one discriminant function in order to identify gray-class samples in each stage. This greatly simplifies the model generation process, compared with the prior art method that requires two special discriminant functions in order to determine the gray zone.

Furthermore, if the gray zone is determined by providing a safety margin on each side of the maximum and minimum discriminant scores of the misclassified training samples, the reliability of the classification/prediction model can be enhanced. The enhancement of the reliability of the classification/prediction model is a very important factor that contributes to improving the prediction rate when the model is used for the classification/prediction of samples of unknown classes.

BRIEF DESCRIPTION OF THE DRAWINGS

FIG. 5 is a diagram depicting one example of an input data table.

FIG. 6 is a diagram depicting one example of an initial parameter set table.

FIG. 7 is a diagram depicting class-1 samples, class-2 samples, and gray-class samples as classified according to one embodiment of the present invention.

FIG. 9 is a diagram depicting one example of a prediction model storing table.

DESCRIPTION OF EMBODIMENTS

Before describing the best mode of the invention, the principle of the invention will be briefly described below.

Figure 1:
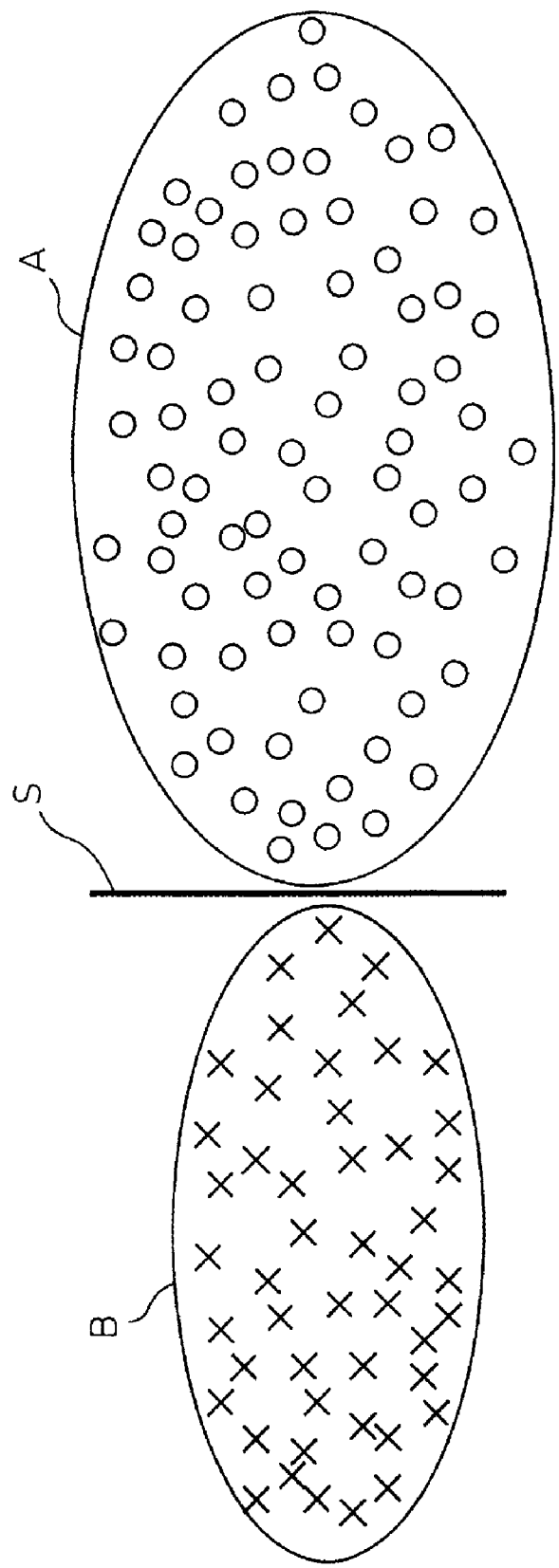
FIG. 1 is a diagram depicting a pattern space obtained as a result of an ideal two-class classification.

FIG. 1 depicts a pattern space obtained as a result of an ideal two-class classification. The term "ideal" means that the classification rate is 100%. In the figure, S indicates a decision surface or hyperplane, and the region A on the right-hand side of the decision surface S is the region A where samples of class 1 are contained (hereinafter called the class-1 region), while the region B on the left-hand side is the region B where samples of class 2 are contained (hereinafter called the class-2 region). Each white dot indicates a sample that normally belongs to class 1, and each X indicates a sample that normally belongs to class 2.

In the ideal two-class classification, that is, when the classification rate is 100%, the samples of class 1, indicated by white dots, and the samples of class 2, indicated by Xs, lie on the respectively designated sides of the decision surface S, and the class-1 region A and the class-2 region B do not overlap each other. On the other hand, in a conventional two-class classification, the regions A and B partly overlap each other.

Figure 2:
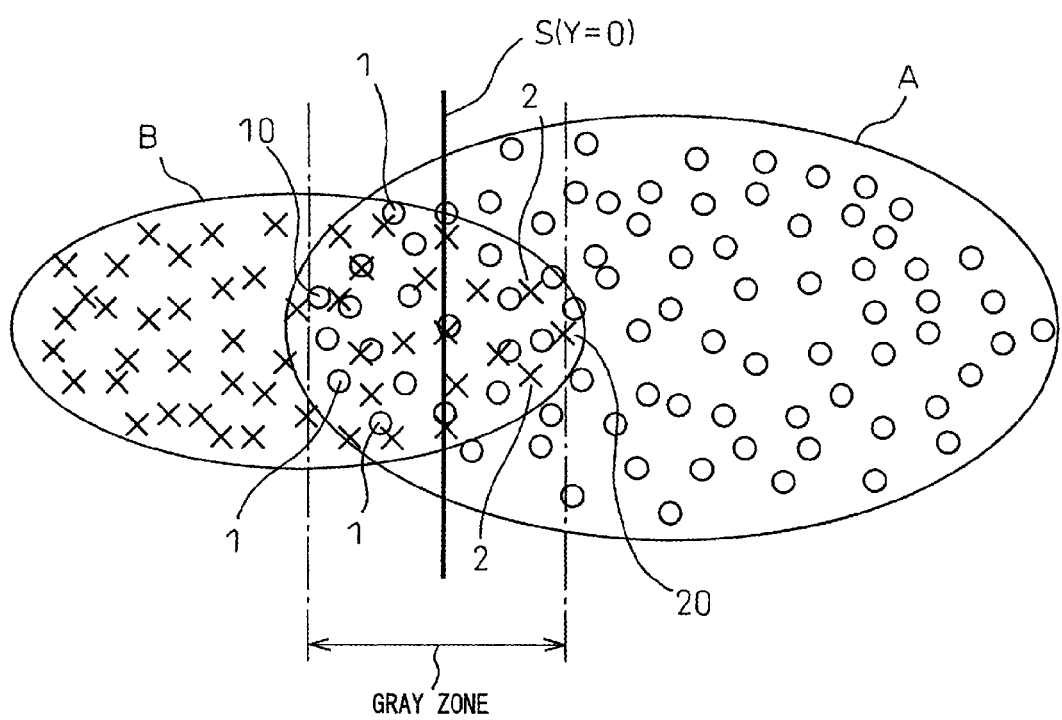
FIG. 2 is a diagram depicting a pattern space obtained as a result of a two-class classification where the classification rate falls short of 100%.

FIG. 2 depicts a pattern space obtained as a result of the conventional two-class classification. When the classification rate falls short of 100%, some of the samples normally belonging to class 1 overlap into the class-2 region and are classified as class-2 samples 1, 1, . . . , and some of the samples normally belonging to class 2 overlap into the class-1 region and are classified as class-1 samples 2, 2, . . . . These wrongly classified samples are called the misclassified samples, and the samples other than the misclassified samples are called the correctly classified samples. The misclassified samples include samples normally belonging to class 1 as well as samples normally belonging to class 2.

The prior art classification technique has attempted to achieve a high classification rate by generating a discriminant function, such as depicted in FIG. 1, that can minimize the occurrence of misclassified samples, but a discriminant function capable of achieving a perfect classification is difficult to generate, and the difficulty rapidly increases as the number of samples increases. The KY method takes an entirely different approach than such a prior art method. That is, in the KY method, the pattern space is divided into three regions, i.e., a region that only contains correctly classified samples, a region that only contains misclassified samples, and a region or a gray zone that contains correctly classified samples and misclassified samples in a mixed manner; then, a new training sample set is formed by grouping together the samples contained in the mixed region (gray zone), and a new discriminant analysis is performed on this training sample set, the above sequence of operations being repeated thereafter. In this case, samples correctly classified in each stage are assigned to the correct classes. By repeating this process, all of the samples can eventually be classified into the correct classes.

Therefore, an important issue in the KY method is how the correctly classified sample regions and the gray zone can be separated from each other. In the technique previously proposed by the present inventor, two special discriminant functions, referred to as the AP model and the AN model, that have just the opposite classification characteristics to each other are used in order to separate the correctly classified sample regions and the gray zone from each other.

The discriminant function (model) Y is given by the following equation (1).

$$Y = a1x1 \pm a2x2 \pm \ldots \pm anxn \pm C \qquad (1)$$

In the above equation (1), Y is the objective variable, x1, x2, . . . , xn are explanatory variables (parameters), a1, a2, . . . , an are weighting coefficients, and C is a constant. The explanatory variables, x1, x2, . . . , xn, have values different for different samples, while the weighting coefficients, a1, a2, . . . , an, have values common to all the samples. Usually, the weighting coefficients are chosen so that the value of the objective variable becomes positive for a sample belonging to class 1 and negative for a sample belonging to class 2. In this case, the decision surface S indicates the plane (hyperplane) where the value of Y is 0.

By substituting the explanatory variables (parameters), x1, x2, . . . , xn, obtained for each sample into the discriminant function (1), the value of the objective variable, Y(1), Y(2), . . . , Y(k), . . . , Y(n), is found for each sample. In the discriminant analysis, the value Y(k) is defined as the "objective variable" or "dependent variable," but when it is viewed as numerical data, it indicates a "discriminant score" which is a continuous variable. The discriminant score indicates how far the sample is located from the decision surface S in the pattern space. The present invention considers the use of this discriminant score to isolate the gray zone.

Usually, in the two-class classification, the discriminant function is constructed so that the value of the discriminant score becomes positive for a sample belonging to class 1 and negative for a sample belonging to class 2, and the absolute magnitude of the discriminant score is not used as classification information. Accordingly, the class of each sample is determined based only on information as to whether the value of the discriminate score is positive or negative. In this way, in the discriminant analysis, the magnitude (absolute value) of the discriminant score is by no means a measure of the intensity of the characteristic of the classification target.

However, the discriminant function for calculating the discriminant score Y is constructed based on the relative positional relationship in the sample space formed from a plurality of samples. Therefore, the discriminant score which is a measure of the distance from the decision surface (hyperplane) carries not only information concerning the distance relationship but also information concerning the complex relative positional relationship between the plurality of samples. Since the discriminant score is calculated from equation (1) using the values of the parameters identifying each sample, it follows that the relationship between each sample is fixedly determined by the discriminant score Y(k). As a result, the objective variable information which was originally simple two-class symbol information (for example, +/−, ½, etc.) becomes a sophisticated information source that provides information in which the relative magnitude of the discriminant score defines the relative positional relationship between each sample.

As depicted in FIG. 2, the misclassified samples 1 and 2 tend to cluster in the vicinity of the decision surface S. That is, the misclassified samples 1 and 2 tend to occur in the region where the distance of each sample from the decision surface S is small. As the distance from the decision surface S increases, the frequency of occurrence of misclassified samples decreases. The discriminant score represents the distance of each sample from the decision surface S; therefore, it is believed that as the discriminant score increases in absolute terms, the frequency of occurrence of misclassified samples decreases. That is, from the point of view of sample pattern space, the discriminant score may be considered a measure of the likely correctness of the classification.

Accordingly, the misclassified-sample region can be determined based on the largest and smallest discriminant scores taken from among the discriminant scores of the misclassified samples. When the gray zone which contains correctly classified samples and misclassified samples in a mixed manner is seen in terms of the discriminant score, it can be seen from FIG. 2 that the region lying between the sample 10 having the smallest discriminant score among the class-1 samples indicated by white dots and the sample 20 having the largest discriminant score among the class-2 samples indicated by Xs is the gray zone that contains correctly classified samples and misclassified samples in a mixed manner.

Figure 3:
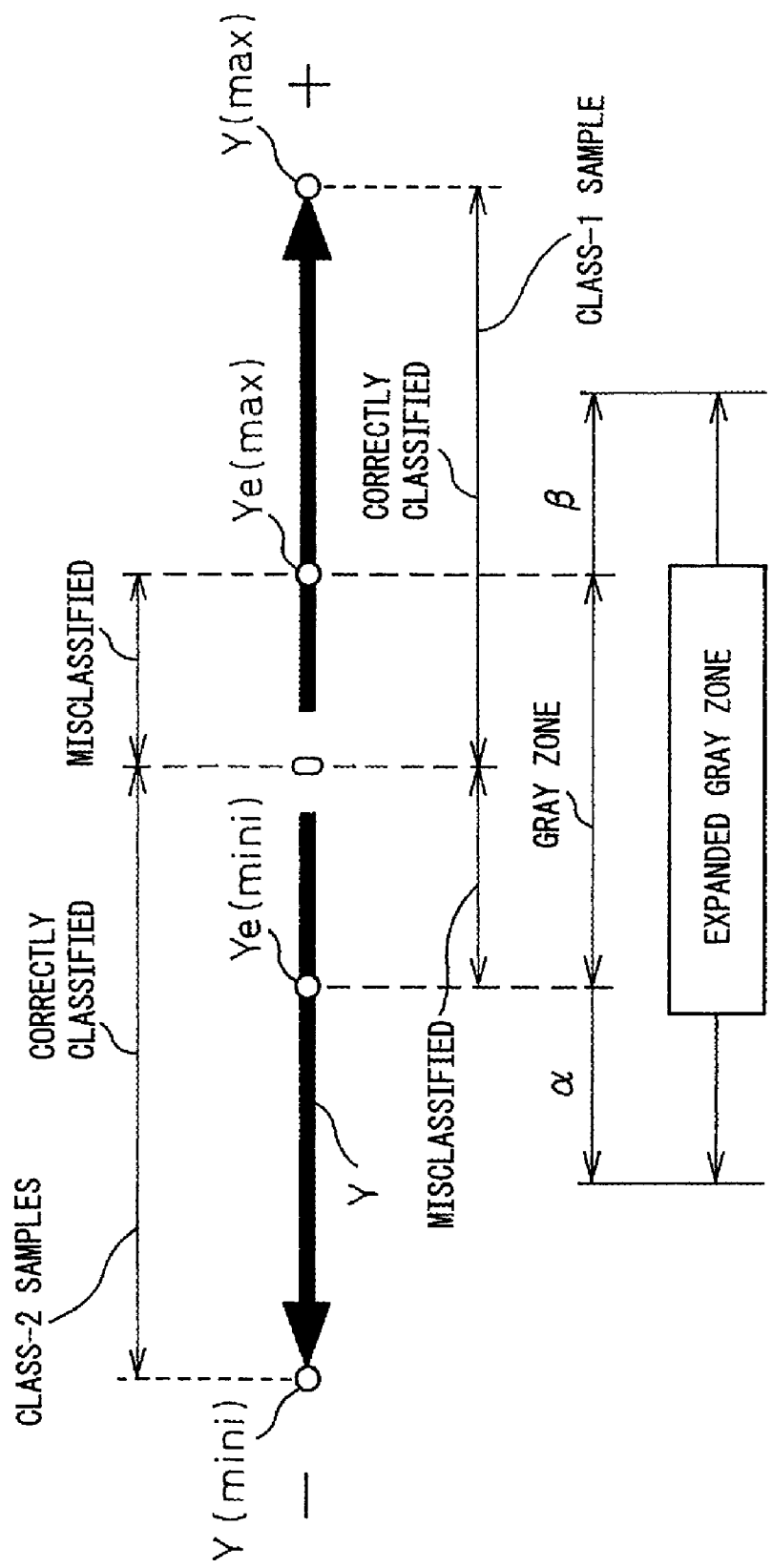
FIG. 3 is a diagram depicting the basic principle of how a gray zone is determined using a two-class classification/prediction model according to the present invention.

FIG. 3 depicts how the samples are sorted by discriminant score Y. The discriminant scores of the samples lie on the straight line Y that extends along the range from the maximum Y (max) to the minimum Y (mini). The discriminant score Y is 0 on the decision surface, and the discriminant score Y may normally become positive for all the class-1 samples, but the value is negative for misclassified samples. Likewise, the discriminant score Y may normally become negative for all the class-2 samples, but the value is positive for some samples that are misclassified. As can be seen from FIG. 3, when seen in terms of the discriminant score, the gray zone that contains correctly classified samples and misclassified samples in a mixed manner is the region bounded by the sample having the smallest discriminant score Ye (min) among the misclassified class-1 samples and the sample having the largest discriminant score Ye (max) among the misclassified class-2 samples.

More specifically, the gray zone is the region where the discriminant score Y lies within the range defined by $$Ye(\min) \leq Y \leq Ye(\max) \qquad (2)$$

and all the correctly classified and misclassified samples contained in this region are the gray-class samples.

Accordingly, the two-class classification is performed on the training samples, and the classification/prediction of each sample is performed using the discriminant function, to identify any misclassified sample. At the same time, the samples are sorted based on their discriminant scores, and the largest discriminant score Ye (max) and the smallest discriminant score Ye (min) are identified from among the misclassified samples; then, the samples whose discriminant scores Y lie within the range defined by Ye(min)≦Y≦Ye(max) are extracted and assigned to the gray zone. After the gray-zone samples have been identified in this manner, these samples are grouped together to form a new training sample set, and the two-class classification in the next stage is performed.

To enhance the reliability of the gray zone, the gray zone of FIG. 3 may be expanded by α and β in the negative and positive directions, to form an expanded gray zone. In this case, the samples contained in the expanded gray zone are extracted and added to the set of samples assigned to the gray zone, and the resulting sample set is used as the new training sample set; in this way, the reliability of the classification can be further enhanced. This means that in the regions that may normally be set as the correctly classified sample regions, regions near the gray zone containing the misclassified sample are tentatively incorporated into the misclassified-sample region and only the regions that definitely contain only the correctly classified samples are set as the correctly classified sample regions; this has the effect of potentially increasing the prediction rate.

As described above, in the present embodiment, the gray zone is formed based on the discriminant scores of the samples obtained by a single discriminant function. As a result, the generation of the model is greatly simplified compared with the case where the gray zone is formed using two discriminant functions AN and AP having special classification characteristics.

Figure 4A:
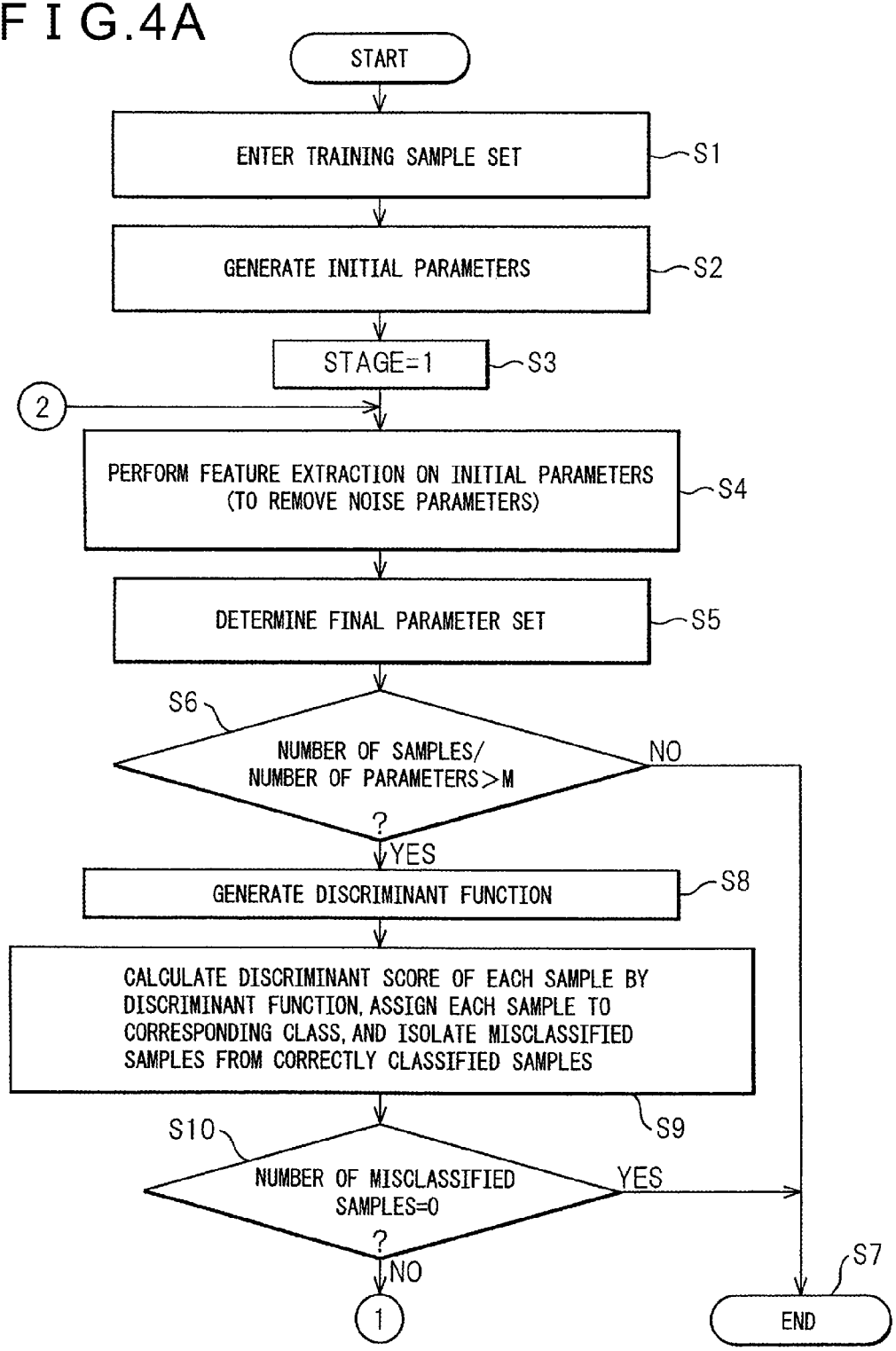
FIG. 4A is a flowchart illustrating the first half of a procedure for implementing a two-class classification/prediction model generation method according to one embodiment of the present invention.
Figure 4B:
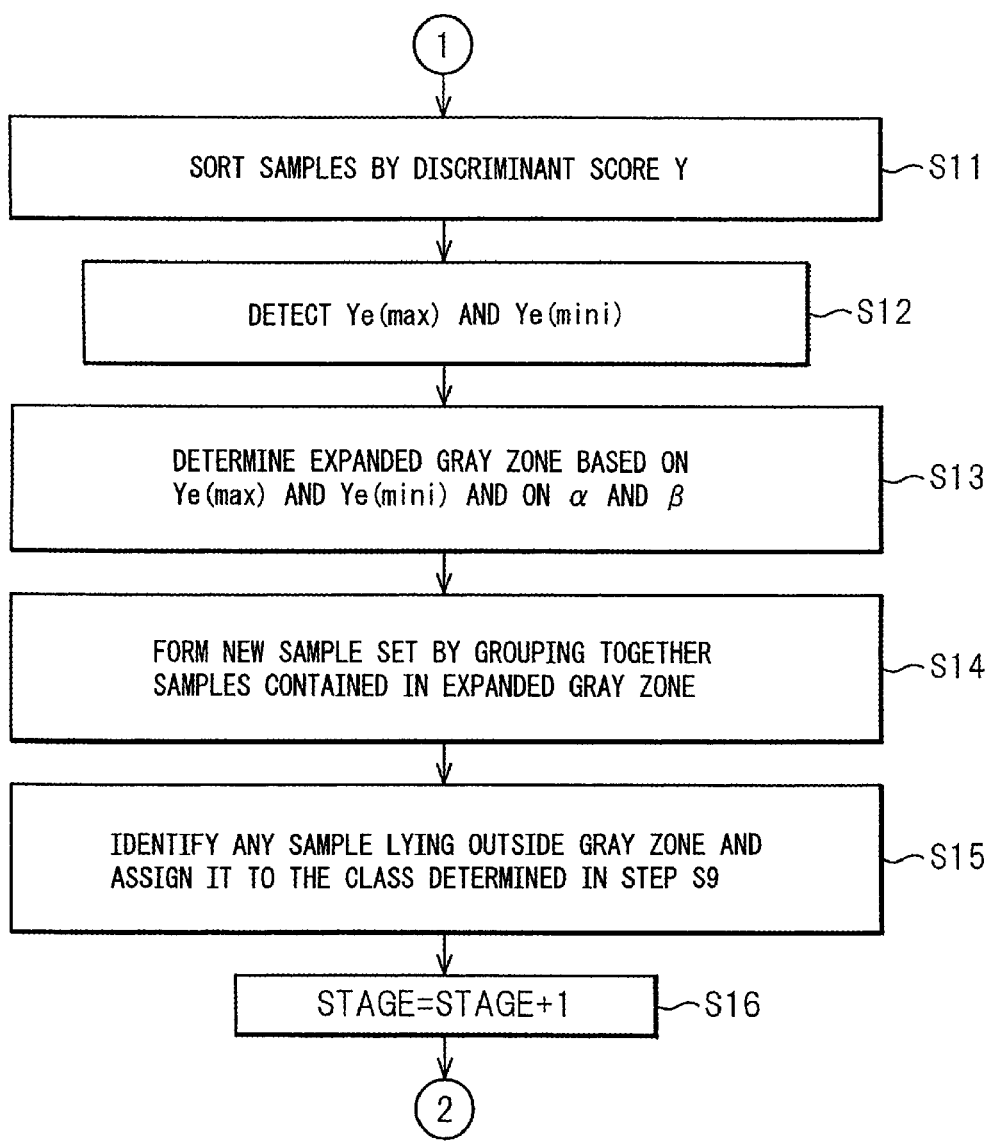
FIG. 4B is a flowchart illustrating the second half of the procedure as a continuation of FIG. 4A.

FIGS. 4A and 4B are a flowchart illustrating the procedure of a classification/prediction model generation method according to one embodiment. First, a plurality of samples whose values for the target characteristic are known are prepared. For example, 500 samples known to have a certain kind of toxicity, i.e., positive samples, and 500 samples known not to have that toxicity, i.e., negative samples, are prepared. The thus prepared samples are entered into a classification/prediction model generating apparatus (step S1), and a table for storing sample data, such as depicted in FIG. 5, is constructed.

In FIG. 5, column 50 indicates the two- or three-dimensional structural formula of each chemical as a sample. Column 51 indicates the CAS number of each chemical, and column 52 indicates the result of the Ames test. In column 52, "mutagen" means that the Ames test result indicates that the sample has mutagenicity (+), while "nonmutagen" means that the sample does not have mutagenicity (−). The illustrated example depicts the data table used to classify the samples into two classes by classifying mutagenic samples as belonging to class 1 (positive class) and nonmutagenic samples as belonging to class 2 (negative class). Column 53 indicates the sample number.

Next, in step S2 of FIG. 4A, initial parameters, i.e., explanatory variables (x1, x2, . . . , xx) for calculating objective variables, are generated. The initial parameters can be automatically generated from the structure of each chemical. For example, ADMEWORKS-ModelBuilder (registered trademark) marketed by Fujitsu can generate thousands of parameters based on the two- or three-dimensional structural formulas and various properties of chemicals. Alternatively, an externally generated parameter set may be taken in and used in combination with the parameter set earlier generated from the structural formula, or only the externally generated parameter set may be used in the above step before proceeding to the next step. In step S3, STAGE is set to 1 to initiate STAGE 1, a first stage of the classification/prediction model generation.

In step S4, feature extraction is performed on the thus generated initial parameters to remove noise parameters unwanted for classification purposes. The final parameter set (x1, x2, . . . , xn) is thus determined (step S5). The feature extraction can be performed using known techniques such as the frequency of occurrence of parameters, the presence or absence of missing parameters, the simple correlation coefficient method, multiple correlation coefficient method, Fischer ratio, variance method, variance weight method, and various other approaches based on genetic algorithms. Various engines for feature extraction are also commercially available.

FIG. 6 is a table depicting the final parameter set selected, as a result of the feature extraction, as having significant effects on the classification/prediction of Ames test results, and numerical data of each individual chemical for the respective parameters. Column 60 indicates the structural formula of each chemical, and column 61 and subsequent columns indicate the various parameters. For example, column 61 indicates the molecular mass of each chemical, column 62 indicates the molecular surface area, and column 63 indicates the value of log P, as the respective parameters. In the data table, the value carried in cell 64 is data indicating the molecular mass of sample 1, the value in cell 65 is data indicating the molecular surface area of sample 1, and the value in cell 66 is data indicating the value of log P of sample 1. The values carried in the respective cells provide the parameter data for the corresponding sample. Column 64 indicates the sample number of each sample.

In step S6, the number of final parameters determined in step S5 is compared with the number of samples, to determine whether or not [the number of samples]/[the number of final parameters] is larger than a predetermined value M. That is, it is determined whether the following relation is satisfied or not.

$$[\text{Number of samples}]/[\text{Number of final parameters}] > M \quad (3)$$

M has a value of about 4 such that if M is not larger than this value, the significance of data analysis will be lost. Accordingly, if NO in step S6, the process proceeds to step S7 to terminate the procedure.

If YES in step S6, the discriminant function 1 for the first stage is generated (step S8) by performing discriminant analysis using the final parameter set determined in step S5. In the discriminant analysis, the discriminant function differs for each different data analysis technique, but generally, the discriminant function is expressed by the earlier given equation (1).

In step S9, the discriminant score of each sample is calculated using the thus generated discriminant function and checked to determine whether the sample is correctly classified or not. The discriminant score Yk of the k-th sample is calculated as $$Yk = a1xk \pm a2x2k \pm \ldots \pm anxnk \pm C \quad (4)$$

Parameter data, x1$k$, x2$k$, . . . , xnk are parameter data (explanatory variable data) for the k-th sample, and a1, a2, a3, . . . , an are the weighting coefficients of the respective parameters. Const is a constant.

Parameter data x11, x21, x31, etc., are obtained from the data carried in the respective cells in FIG. 6. Accordingly, when the coefficients a1, a2, etc., of the respective parameters are obtained by the discriminant analysis, the discriminant score Yk of the k-th sample is calculated by substituting the data carried in the respective cells of the table of FIG. 6 into the equation (4). If the unit of the parameter value differs greatly for each kind of parameter, the cell values may be converted by such operations as auto scaling and the thus converted values may be used as the cell data.

The sample is classified according to the sign (positive or negative) of the calculated value Yk. In the present embodiment, the discriminant function is constructed so that the value of Y becomes negative in the case of nonmutagen and positive in the case of mutagen. If the value of the discriminant score Yk is positive, the sample is assigned to class 1 (positive), but if the value of the discriminant score Yk is negative, the sample is assigned to class 2 (negative). Various engines for performing discriminant analysis are also commercially available.

When the discriminant score Yk of the sample k is calculated, the calculated value is compared with the inherent characteristic value of the sample Yk to determine whether the sample is correctly classified or not. For example, if the value of the discriminant score Y1 calculated for sample 1 in FIG. 5 is negative, it can be determined that the sample is correctly classified, since it can be seen from column 52 that the Ames test result for this sample is negative. On the other hand, if the value of the discriminant score Y3 calculated for sample 3 is positive, it can be determined that the sample is misclassified, since it can be seen from column 52 that the Ames test result for this sample is negative.

After the classification results of all the samples have been checked, the process proceeds to step S10 in FIG. 4A to determine whether there is any misclassified sample. If there is no misclassified sample (YES in step S10), it is considered that all the samples have been correctly classified by the discriminant function 1; therefore, the process proceeds to step S7 to terminate the procedure. If there is any misclassified sample (NO in step S10), the process proceeds to step S11 in FIG. 4B where all the samples are sorted based on their discriminant scores. In step S12, based on the results of the sorting according to the discriminant score, the largest discriminant score Ye (max) and the smallest discriminant score Ye (min) are determined among the misclassified samples.

In step S13, the gray zone or the expanded gray zone is determined based on the largest discriminant score Ye (max) and the smallest discriminant score Ye (min) of the misclassified samples determined in step S11 and on the predetermined safety margins $\alpha$ and $\beta$. Information concerning the gray zone is stored as model information for STAGE 1 together with the discriminant function 1.

The safety margins $\alpha$ and $\beta$ are set, for example, in the following manner. That is, as depicted in FIG. 3, $\alpha$ is set, for example, equal to 50% of the difference between the minimum value Ye (min) of the discriminant score in the gray zone and the minimum value Y (min) of the discriminant score taken from among all the samples. Similarly, β is set, for example, equal to 50% of the difference between the maximum value Ye (max) of the discriminant score in the gray zone and the maximum value Y (max) of the discriminant score taken from among all the samples. As α and β are made larger, the reliability of the classification/prediction model according to the method of the embodiment improves, but conversely, since the number of samples contained in the gray zone increases, the number of STAGEs (stages) correspondingly increases, as a result of which the amount of work that has to be expended in generating the model increases, and the computation time for the prediction also increases.

For maximum reliability, α and β may be set so that the gray zone is bounded by the discriminant score of the sample having the second smallest discriminant score next to the sample having the smallest discriminant score of all the samples and the discriminant score of the sample having the second largest discriminant score next to the sample having the largest discriminant score of all the samples. In this case, all the samples, excluding only the two samples having the smallest discriminant score and the largest discriminant score, respectively, are identified as samples belonging to the expanded gray zone.

When the expanded gray zone is determined in step S13 of FIG. 4B, then in step S14 the samples (gray-class samples) contained in the expanded gray zone are grouped together to form a new sample set. Both the correctly classified and misclassified samples in step S9 are contained in the gray zone. When the expanded gray zone is determined, then in step S15 any sample lying outside the expanded gray zone is identified and assigned to the group determined in step S9. As a result, at the end of step S15, the training sample set is classified into three classes, i.e., the samples belonging to class 1, the samples belonging to class 2, and the samples belonging to the expanded gray zone (gray class). Step S15 is not needed when generating a classification/prediction model for purely unknown samples.

FIG. 7 depicts the class-1 samples, class-2 samples, and gray-class samples assigned to the respective classes in step S15 and plotted on the pattern space of FIG. 2. That is, FIG. 7 depicts the results of STAGE 1.

When the results of STAGE 1 are obtained as described above, STAGE is incremented by 1 in step S16, and the process returns to step S4 in FIG. 4A to initiate the discriminant analysis of STAGE 2 by using the new sample set formed in step S14, i.e., by taking the gray-class sample set as a new training sample set. As in the case of STAGE 1, by performing the process from step S4 to step S15, the class-1 samples, class-2 samples, and gray-class samples in STAGE 2 are identified. When the gray-class samples are identified, the process from step S4 onward is repeated, and the class-1 samples, class-2 samples, and gray-class samples in STAGE 3 are identified. The safety margins α and β may be set the same for all STAGEs or may be set differently for each STAGE.

The iterative loop from step S4 to step S15 is repeated until the ratio of the number of samples to the number of parameters becomes smaller than the predetermined value M (NO in step S6) or until the number of misclassified samples becomes zero in step S10. If the process is terminated in step S10, this means that all the initial training samples have been classified into the correct classes, achieving a classification rate of 100%.

Figure 8:
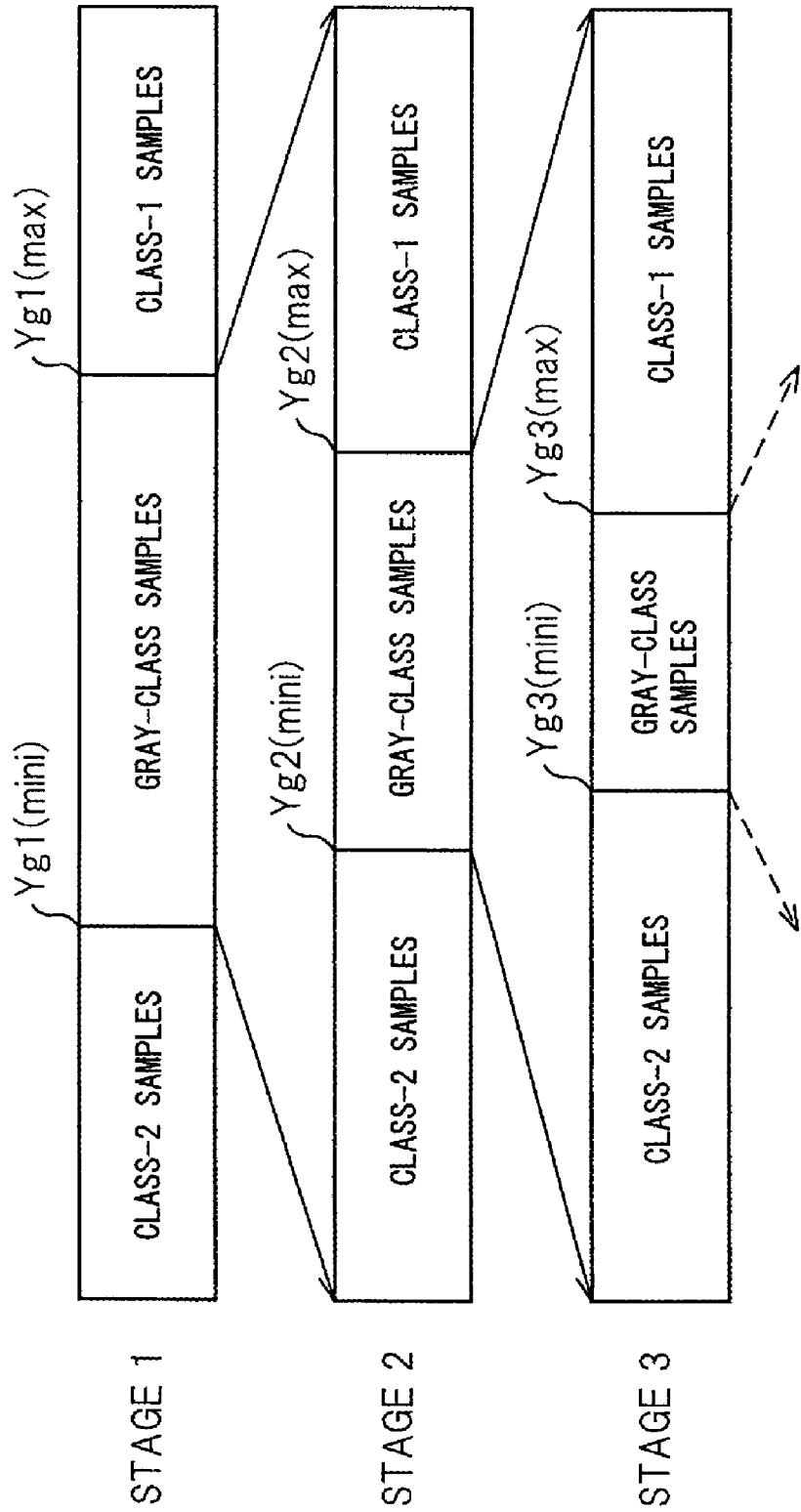
FIG. 8 is a diagram explaining how the gray-class samples are classified stage by stage according to one embodiment of the present invention.

FIG. 8 is a diagram conceptually illustrating the process from STAGE 1, for example, to STAGE 3. From this figure, it can be easily understood that the training sample set in STAGE 2 is constructed from the samples identified as gray-class samples in STAGE 1, and that the training sample set in STAGE 3 is constructed from the samples identified as gray-class samples in STAGE 2. This process is repeated until the number of gray-class samples decreases to 0. In FIG. 8, Yg1(mini), Yg2(mini), Yg1(max), Yg2(max), etc., are discriminant score information that defines the gray zone (or the expanded gray zone), and these pieces of information are stored together with the discriminant function for each stage in order to construct the model.

FIG. 9 depicts a table for storing the classification/prediction model constructed using the information obtained in the respective STAGEs. As depicted, the classification/prediction model of the present embodiment is constructed using the discriminant functions 1, 2, ..., n generated in the respective STAGEs and the gray zone information obtained in the respective STAGEs, that is, the smallest and largest discriminant scores, [Yg1(min), Yg1(max)], [Yg2(min), Yg2(max)], ..., [Ygn(min), Ygn(max)], that define the expanded gray zone.

In the first embodiment depicted in FIGS. 4A and 4B, the discriminant analysis in the next STAGE is performed as long as there remains any misclassified sample in step S10. In an alternative embodiment, the number of STAGEs that can be performed may be limited to a predetermined number, and upon completing the predetermined number of STAGEs, the entire process may be terminated regardless of whether there remains any misclassified sample.

In this case, step S16 of FIG. 4B is followed by the step of determining whether the number of STAGEs has reached the predetermined number. In a further alternative embodiment, the program processing time may be limited to a predetermined length of time, with provisions made to forcefully terminate the program when the predetermined length of time has elapsed. With these methods, the model generation process can be forcefully terminated when there is no indication that the number of misclassified samples will ever decrease to 0, for example, due to wrong data or the like contained in the training sample set.

In a still further alternative embodiment, different discriminant analysis techniques may be used for different STAGEs. For example, provisions may be made to use a Bayes discriminant analysis method in STAGE 1 and an AdaBoost method in STAGE 2. It is of course possible to use the same classification method for all STAGEs. Further, the safety margins α and β need not necessarily be set the same for all STAGEs, but can be set as desired for each STAGE.

[Application to Tailor-Made Modeling]

The present inventor proposes a method called tailor-made modeling (non-patent document 2, PCT/JP2007/066286) that constructs a prediction model by efficiently reflecting information for predicting the properties of one unknown chemical compound and that performs the prediction by applying the thus constructed prediction model only to that particular unknown chemical compound. The most important feature of the tailor-made modeling is that one prediction model corresponds to one unknown chemical compound. The prediction model thus constructed contains information important for that particular unknown chemical compound but contains very little noise information. As a matter of course, the prediction rate greatly improves. The effect of the invention can be further enhanced by applying the two-class classification/prediction model generation method, apparatus, or program proposed herein to the tailor-made modeling.

Figure 10:
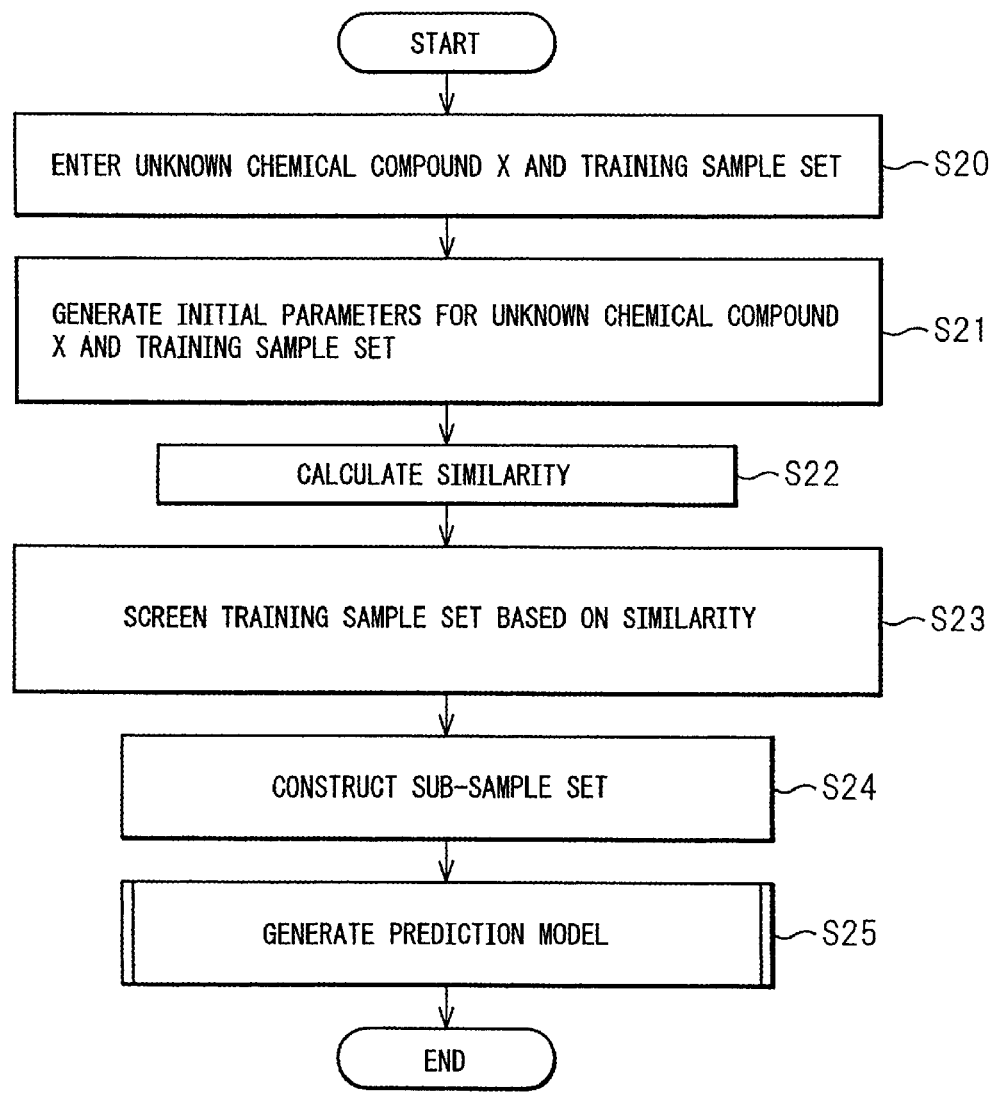
FIG. 10 is a flowchart illustrating an embodiment in which the two-class classification/prediction model generation method according to the present invention is applied to tailor-made modeling.

FIG. 10 is a flowchart illustrating a procedure according to another embodiment in which the tailor-made modeling is implemented by using the two-class classification/prediction model generation method described with reference to FIGS. 4A and 4B. In step S20, an unknown chemical compound X and a training sample set are entered, and in step S21, initial parameters are generated for both of them. In step S22, parameters related to structural similarity are selected from among the initial parameters generated in step S21, and the degree of structural similarity between the unknown chemical compound X and each individual training sample is calculated using the selected parameters. For the calculation of the structural similarity, for example, a Tanimoto coefficient, Euclidean distance, cosine coefficient, Pearson's product-moment correlation coefficient, etc., may be used.

In step S23, for the unknown chemical compound X and each individual training sample, screening of the training sample set is performed using a predetermined similarity threshold value, and training samples similar in structure to the unknown chemical compound X are extracted to construct a sub-sample set (step S24). In the tailor-made modeling, since the sub-sample set containing samples similar in structure to the unknown chemical compound X is constructed, and a classification/prediction model is generated by performing a two-class classification on the sub-sample set, it is possible to construct a model having high prediction reliability for the unknown chemical compound X.

Step S25 is a routine for generating a prediction model based on the sub-sample set, and corresponds to the process starting from step S3 in FIGS. 4A and 4B. By carrying out step S25, a prediction model having a high degree of significance for the unknown chemical compound X can be generated in a simple procedure. In step S25, a good-quality sample set optimum for the classification/prediction of the target sample is used. If the "KY method" or the classification method according to the present invention is applied in this stage, a classification rate of 100% can always be ensured, and the prediction model thus constructed achieves a very high prediction rate.

[Classification/Prediction of Samples of Unknown Classes]

Figure 11:
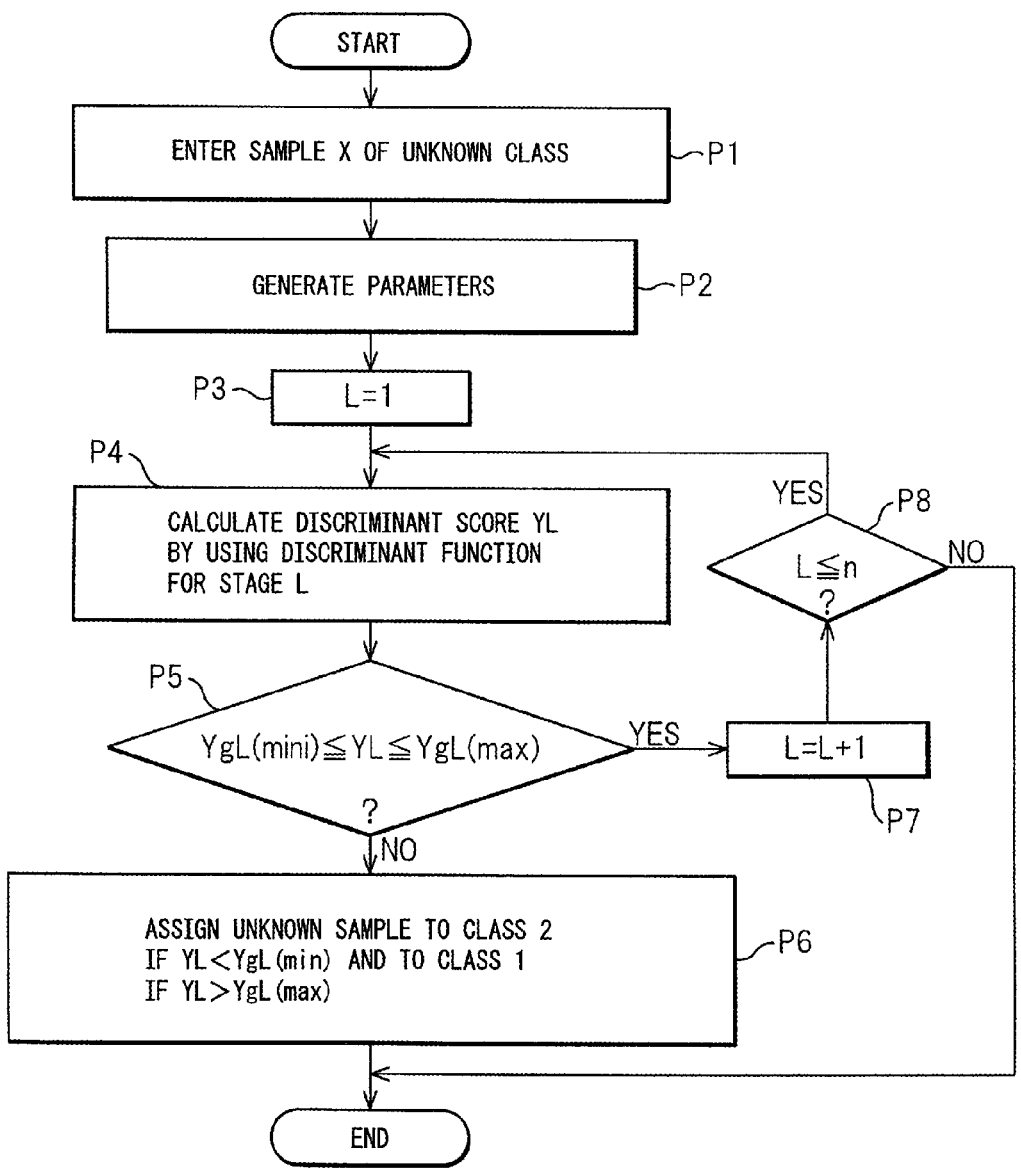
FIG. 11 is a flowchart illustrating a procedure for performing the classification/prediction of unknown samples by using the prediction model generated by the method of the present invention.

FIG. 11 is a flowchart illustrating a process for performing the classification/prediction of samples of unknown classes by using the two-class classification/prediction model (for example, see FIG. 9) generated in any one of the above embodiments. In step P1, a sample X of unknown class is entered, and in step P2, parameters are generated for the unknown sample X. In step P3, STAGE L is set to STAGE 1 (L=1). In step P4, the discriminant score Y1 of the unknown sample X is calculated by using the discriminant function 1 for STAGE 1.

In step P5, the gray class information for STAGE 1 is acquired, and the discriminant score Y1 of the unknown sample X is compared with it. If Y1 falls within the range bounded by the smallest discriminant score Yg1(min) and the largest discriminant score Yg1(max) in the expanded gray zone, i.e., if YES in step P5, the unknown sample X is assigned to the gray class in STAGE 1. On the other hand, if NO in step P5, it is determined that the unknown sample X is not a gray-class sample, and in step P6, the unknown sample X is assigned to class 2 if the discriminant score Y1 is smaller than Yg1(min) and to class 1 if the discriminant score Y1 is larger than Yg1(max); after that, the process is terminated.

If the unknown sample X is assigned to the gray class in step P5, then the current STAGE is incremented by 1 (L=L+1) in step P7, and after confirming in step P8 that the STAGE thus incremented does not exceed the final STAGEn (L≦n) (YES in step P8), the process returns to step P4 to perform the classification of the unknown sample X by using the discriminant function and gray zone information for the next STAGE 2. The classification/prediction of the sample of unknown class is performed by repeating the above process. If the classification/prediction of the sample X is not completed even when the STAGE has exceeded the final STAGEn (YES in step P8), the process is terminated.

[System Configuration]

Figure 12:
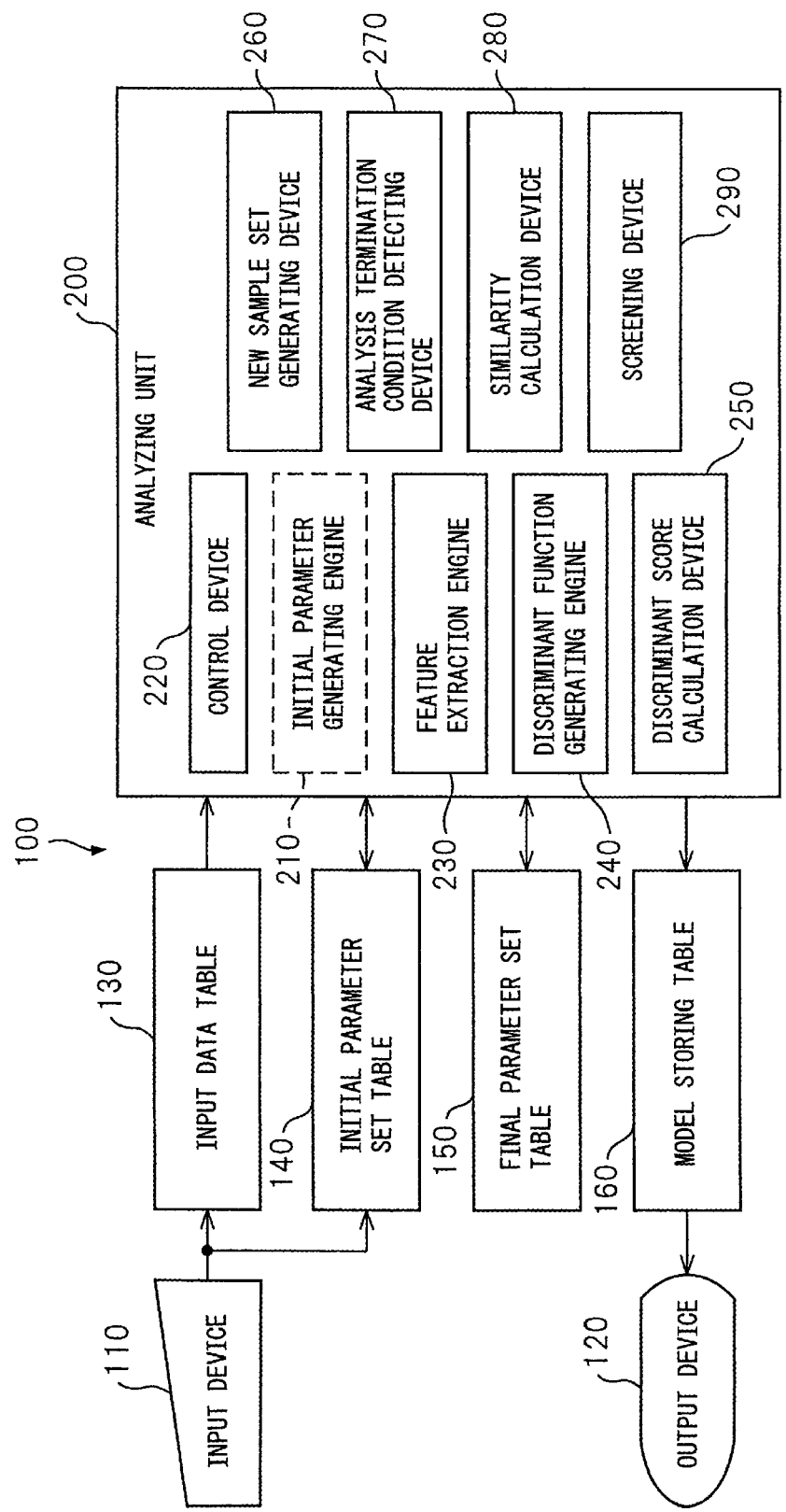
FIG. 12 is a diagram depicting the system configuration of a classification/prediction model generating apparatus according to one embodiment of the present invention.

FIG. 12 is a block diagram depicting the system configuration of a two-class classification/prediction model generating apparatus according to one embodiment. The two-class classification/prediction model generating apparatus 100 according to the present embodiment includes an input device 110 for entering sample data and an output device 120 for outputting the classification results or the data being processed. Sample information for classification training is entered from the input device 110 and stored in an input data table 130. When the sample is a chemical compound, the two- or three-dimensional structural formula of the chemical compound and its known objective variable value are entered from the input device 110 and stored in the input data table 130.

Initial parameter set data may be entered via the input device 110 and stored in an initial parameter set table 140. If an analyzing unit 200 has an engine 210 for automatically generating the initial parameters for input samples, there is no need to enter the initial parameter set data from the input device 110.

In FIG. 12, reference numeral 150 is a final parameter set storing table for storing the final parameter set obtained by performing feature extraction on the initial parameter set. Further, reference numeral 160 is a model storing table for storing the two-class classification/prediction model, i.e., the discriminant function and gray zone information determined for each STAGE.

When applying the apparatus of the present embodiment to the tailor-made modeling, the apparatus is provided with a similarity calculation device 280 for calculating structural similarity and a screening device 290 for screening the initial training sample set based on the calculated similarity.

The analyzing unit 200 includes a control device 220, an initial parameter generating engine 210, a feature extraction engine 230, a discriminant function generating engine 240, a discriminant score calculation device 250, a new sample set generating device 260, and an analysis termination condition detecting device 270. The analyzing unit 200 may further include the similarity calculation device 280 and screening device 290. If provisions are made to generate the initial parameters outside the apparatus, the initial parameter generating engine 210 is not needed. The initial parameter generating engine 210 and the feature extraction engine 230 can be implemented using existing ones.

The feature extraction engine 230 determines the final parameter set by performing feature extraction on the initial parameter set, and stores it in the final parameter set table 150. The discriminant function generating engine 240 includes various known discriminant analysis engines and, using the discriminant analysis engine specified by the user or suitably selected by the system, generates the discriminant function by performing the discriminant analysis of the input sample while referring to the final parameter set table 150. The discriminant score calculation device 250 calculates the discriminant score of each sample by entering the parameters of the sample into the discriminant function generated by the discriminant function generating engine 240. The new sample set generating device 260 generates a new sample set by setting the expanded gray zone in accordance with the algorithm illustrated with reference to FIGS. 2 and 3 and by identifying the samples contained in this zone.

The feature extraction engine 230, the discriminant function generating engine 240, the discriminant score calculation device 250, and the new sample set generating device 260 operate under the control of the control device 220 to carry out the process illustrated in FIGS. 4A and 4B. The analysis termination condition detecting device 270 has the function of terminating the classification/prediction model generation process by detecting the instant that the number of samples in the gray class has decreased to substantially zero. If the number of samples in the gray class does not decrease to zero for any reason, the analysis termination condition detecting device 270 decides to terminate the process upon detecting that the number of repetitions of the process, i.e., the number of STAGEs, has reached a predetermined number or the processing time has exceeded a predetermined time.

The discriminant function and gray zone information obtained for each STAGE by the analyzing unit 200 are stored in the model storing table 160 or output via the output device 120. The output mode is suitably selected from among output in the form of a file, output on a display, output by printout, etc.

When performing the tailor-made modeling, a sub-sample set is constructed by operating the similarity calculation device 280 and screening device 290 in accordance with the procedure illustrated in FIG. 10.

Each of the above programs can be stored on a computer-readable recording medium which comprises all computer-readable media except for a transitory, propagating signal, and such recording media can be distributed and circulated for use. Further, each of the above programs can be distributed and circulated through communication networks such as the Internet. The computer-readable recording media include magnetic recording devices, optical disks, magneto-optical disks, or semiconductor memories (such as RAM and ROM). Examples of magnetic recording devices include hard disk drives (HDDs), flexible disks (FDs), magnetic tapes (MTs), etc. Examples of optical disks include DVDs (Digital Versatile Discs), DVD-RAMs, CD-ROMs, CR-RWs, etc. Example of magneto-optical disks include MOs (Magneto-Optical discs).

INDUSTRIAL APPLICABILITY

The present invention is applicable to any industrial field to which two-class classification can be applied. The main applicable fields are listed below.
1) Chemical data analysis
2) Biotechnology-related research
3) Protein-related research
4) Medical-related research
5) Food-related research
6) Economy-related research
7) Engineering-related research
8) Data analysis aimed at improving production yields, etc.
9) Environment-related research In the field of the chemical data analysis 1), the invention can be applied more particularly to the following researches.
 (1) Structure-activity/ADME/toxicity/property correlation research
 (2) Structure-spectrum correlation research
 (3) Metabonomics-related research
 (4) Chemometrics research For example, in the environment and drug development research fields, the structure-toxicity correlation research is gaining importance, and it is important to predict, for example, Ames test results. The reason is that the Ames test is incorporated as one of the most important items into national-level chemical regulations, such as industrial safety and health law and chemical examination law related to toxic chemicals regulations. Any chemical to be marketed must pass the Ames test; otherwise, the chemical cannot be manufactured in Japan, and the manufacturing activities of chemical companies would halt. Manufacturing overseas and exporting such chemicals are banned by safety regulations adopted in the countries concerned.

For example, according to the European Union's REACH regulation, which entered into force on June 2007, any company that manufactures or uses a chemical is obliged to predict and evaluate the Ames test result of that chemical. The present invention provides a very useful tool for the prediction of such test results. The Ames test is one of the mutagenesis tests developed by Dr. Ames, USA, and provides a simple method for testing carcinogenicity. It is therefore adopted worldwide as one safety test for measuring the safety of many chemicals and products using chemicals.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

The invention claimed is:

1. A method for generating a two-class classification/prediction model, comprising:
 obtaining a discriminant function to classify a training sample set into two predetermined classes on a basis of an explanatory variable generated for each individual training sample contained in said training sample set;
 calculating a discriminant score for each training sample by using said obtained discriminant function;
 determining, based on said calculated discriminant score, whether said training sample is correctly classified;
 determining a misclassified-sample region based on maximum and minimum discriminant scores taken from among misclassified samples in said training sample set;
 constructing a new training sample set by extracting said training samples contained in said misclassified-sample region;
 repeating said obtaining, said calculating, said determining of said training sample, and said determining of said misclassified-sample region, for said new training sample set; and
 storing, as a two-class classification/prediction model for samples of unknown classes, a plurality of discriminant functions obtained as a result of said repeating and misclassified-sample region information associated with each of said discriminant functions.

2. The method according to claim 1, wherein said misclassified-sample region in said determining said misclassified-sample region, is determined by adding an arbitrary safety margin on each side of said maximum and minimum discriminant scores taken from among said misclassified training samples.

3. The method according to claim 1, wherein when the number of misclassified training samples in said determining based on said calculated discriminant score is zero, the subsequent processing is not performed.

4. The method according to claim 1, wherein said repeating occurs a predetermined number of times.

5. The method according to claim 1, wherein said each individual training sample is a chemical compound, and said two predetermined classes include a class of chemical compounds having a given toxicity and a class of chemical compounds not having said toxicity.

6. The method according to claim 1, comprising removing unnecessary explanatory variables by performing feature extraction on said explanatory variables generated for said training sample set.

7. The method according to claim 6, wherein said repeating is stopped when a ratio of a number of samples in said training sample set to a number of explanatory variables after said feature extraction has decreased to or below a predetermined value.

8. A non-transitory computer readable medium having a program recorded thereon, said program generating a two-class classification/prediction model by causing a computer to perform a process comprising:
   obtaining a discriminant function to classify a training sample set into two predetermined classes on a basis of an explanatory variable generated for each individual training sample contained in said training sample set;
   calculating a discriminant score for each training sample by using said obtained discriminant function;
   determining based on said calculated discriminant score, whether said training sample is correctly classified or not;
   determining a misclassified-sample region based on maximum and minimum discriminant scores taken from among misclassified samples in said training sample set;
   constructing a new training sample set by extracting said training samples contained in said misclassified-sample region; and
   repeating said obtaining, said calculating, said determining of said training sample, and said determining of said misclassified-sample region, for said new training sample set.

9. The non-transitory computer readable medium according to claim 8, wherein said misclassified-sample region in said determining said misclassified-sample region is determined by adding an arbitrary safety margin on each side of said maximum and minimum discriminant scores taken from among said misclassified training samples.

10. The medium according to claim 8, wherein when the number of misclassified training samples in said determining based on said calculated discriminant score is zero, subsequent processing is not performed.

11. The non-transitory computer readable medium according to claim 8, wherein said repeating occurs a predetermined number of times.

12. The non-transitory computer readable medium according to claim 8, wherein said repeating stops when a predetermined processing time has elapsed.

13. The non-transitory computer readable medium according to claim 8, wherein said each individual training sample is a chemical compound, and said two predetermined classes include a class of chemical compounds having a given toxicity and a class of chemical compounds not having said toxicity.

14. The non-transitory computer readable medium according to claim 8, comprising removing unnecessary explanatory variables by performing feature extraction on said explanatory variables generated for said training sample set.

15. The non-transitory computer readable medium according to claim 14, wherein said repeating is stopped when a ratio of a number of samples in said training sample set to a number of explanatory variables after said feature extraction has decreased to or below a predetermined value.

16. An apparatus having a processor to generate, from a training sample set constructed from a plurality of samples each known to belong to class 1 or class 2, a two-class classification/prediction model to classify an unknown sample which is not known to belong to said class 1 or said class 2, comprising:
   an explanatory variable acquiring device which acquires an explanatory variable for each sample contained in said training sample set;
   a discriminant function generating engine which generates a discriminant function to discriminate between said class 1 and said class 2 by performing discriminant analysis based on said acquired explanatory variable;
   a discriminant score calculation device which calculates a discriminant score for said each sample based on said generated discriminant function;
   a sample set generating device which determines a misclassified-sample region based on said calculated discriminant score, and generates a new sample set by extracting samples contained in said region;
   a control device which causes said explanatory variable acquiring device, said discriminant function generating engine, said discriminant score calculation device, and said sample set generating device, to operate repeatedly by using said generated new sample set as said training sample set; and
   a storage device which stores, as said classification/prediction model, said discriminant function generated by said discriminant function generating engine and information concerning said misclassified-sample region determined by said sample set generating device.

17. The apparatus according to claim 16, comprising a feature extraction engine which performs feature extraction on explanatory variables acquired by said explanatory variable acquiring device, in order to remove any said explanatory variable not necessary for classification.

18. An apparatus having a processor to generate, from a training sample set constructed from a plurality of chemical compounds known to have a given toxicity and a plurality of chemical compounds not known to have said toxicity, a chemical toxicity prediction model for a chemical compound which is not known to have said toxicity, comprising:
   a parameter acquiring device which acquires a parameter for each chemical compound contained in said training sample set;
   a discriminant function generating engine which generates a discriminant function to discriminate the presence or absence of said toxicity by performing discriminant analysis based on said acquired parameter;
   a discriminant score calculation device which calculates a discriminant score for said each chemical compound based on said generated discriminant function;
   a sample set generating device which determines a misclassified-chemical-compound region based on said calculated discriminant score, and generates a new sample set by extracting chemical compounds contained in said region;
   a control device which causes said parameter acquiring device, said discriminant function generating engine, said discriminant score calculation device, and said sample set generating device to operate repeatedly by using said generated new sample set as said training sample set; and a storage device which stores, as said toxicity prediction model, said discriminant function generated by said discriminant function generating engine and information concerning said misclassified-chemical-compound region determined by said sample set generating device.

19. The apparatus according to claim 18, comprising a feature extraction engine which performs feature extraction on parameters acquired by said parameter acquiring device, in order to remove any said parameter not necessary for classification.

20. The apparatus according to claim 18, comprising a screening device which screens said training sample set based on similarity between said unknown chemical compound and each chemical compound contained in said training sample set, and wherein said toxicity prediction model is generated based on the training sample set obtained by said screening.

* * * * *